United States Patent [19]

Conner et al.

[11] Patent Number: 5,292,903
[45] Date of Patent: Mar. 8, 1994

[54] ONE STEP METHOD FOR THE PREPARATION OF DIFURFURYL DIAMINES

[75] Inventors: Anthony H. Conner, Madison; Michael S. Holfinger, Madison; Charles G. Hill, Jr., Madison, all of Wis.; William J. McKillip, Crystal Lake, Ill.; Rolf H. Reimann, Amanzintoti, South Africa

[73] Assignee: The United States Department of Agriculture as represented by the Secretary of Agriculture, Washington, D.C.

[21] Appl. No.: 748,380

[22] Filed: Aug. 22, 1991

[51] Int. Cl.[5] ............................................ C07D 307/40
[52] U.S. Cl. ...................................................... 549/472
[58] Field of Search .......................................... 549/472

[56] References Cited

U.S. PATENT DOCUMENTS

| | | | |
|---|---|---|---|
| 3,945,999 | 3/1976 | Gruffar et al. | 549/472 |
| 4,124,604 | 11/1978 | Yu | 549/472 |
| 4,219,485 | 8/1980 | Dunlop | 549/472 |
| 4,219,487 | 8/1980 | Dunlop | 549/472 |
| 4,496,751 | 1/1985 | Still et al. | 549/472 |
| 4,577,035 | 3/1986 | Hoffmann et al. | 549/472 |

FOREIGN PATENT DOCUMENTS 0004160 7/1987 PCT Int'l Appl. .

Primary Examiner—C. Warren Ivy
Assistant Examiner—A. A. Owens
Attorney, Agent, or Firm—M. Howard Silverstein; John D. Fado; Janet I. Stockhausen

[57] ABSTRACT

A synthetic procedure for the synthesis of diamino difurfuryl compounds via a one-step, low-temperature reaction that does not require additional steps for the protection of the amino functionalities in the reactant or the deprotection of the amino functionalities in an intermediate product to give the final product is disclosed. The importance of acid concentration, reaction temperature, and reaction time to the one step method are disclosed.

14 Claims, 8 Drawing Sheets

ONE STEP METHOD FOR THE PREPARATION OF DIFURFURYL DIAMINES

BACKGROUND OF THE INVENTION

1. Field of the Invention

This invention relates generally to the preparation of difurfuryl diamines. In particular, the invention relates to an improved chemical synthesis from biomass of furan-based diamino compounds having the following general formula:

where

R[1] and R[2]=H, $CH_3$, $CH_3CH_2$, Furan, di-Hydrofuran, and mixtures thereof, or in principle any of a number of other groups or mixture of groups R[3]=Primarily H, but in principle could consist of $CH_3$, $CH_3CH_2$, or any number of other possible groups or mixture of groups.

2. Description of the Prior Art

Compounds used in the production of polymers have traditionally been synthesized from petroleum-based products. However, declining petroleum reserves, accompanied by the increasing price of petrochemicals, have resulted in a search for alternative sources of chemical feedstocks which are both economical and efficient. It is well known that furan compounds may be generated in almost unlimited quantities from renewable resources, including maize, oat husks, and corn cobs. Other renewable resources, such as hardwoods, also may be potential sources of furan compounds.

The principal utility of the furan compounds produced via the one step method disclosed would be for the production of polymeric compounds. In particular, the compounds would be utilized for adhesives and polyurethane production. The compounds have potential as thermoset adhesives for use with wood composite materials and could also be utilized for the synthesis of condensation polymers from difunctional monomers.

The prior art clearly indicates that to condense carbonyl-containing compounds with furfurylamine, the amino function must be protected during the reaction. The formamide derivative proved to be the most effective. Thus, synthesis of the diamino difurfuryl compounds by the method known to those skilled in the art requires several independent reaction steps including the blocking of the amino group in the original reactant and deblocking of the amino groups to yield the final diamine. This leads to a reaction scheme that is both complex and inefficient.

Cawse et al. [*Makromol. Chem.* 185:697-707(1984)], in their article titled "Polymers from renewable sources, 1: Diamines and diisocyanates containing difurylalkane moieties," dislose the preparation of furan-based diisocyanates and diamines as potential polymers for polyamide and polyurethane production. The starting materials were methyl furoate and furfurylaine. A one-step reaction scheme was explored in the article. However, this reaction scheme gave only low yields of an undesired Mannich type product together with other products presumed to be homologous oligomers. It is unclear exactly how this reaction was practiced in the prior art since it was not effective and was thus not reported in detail.

Still et al., U.S. Pat. No. 4,496,751, disclose difunctional furan derivatives. To produce the furan derivatives, the amino functionalities are protected by various compounds prior to coupling with the carbonyl compound.

Leon et al, U.S. Pat. No. 2,681,917, disclose a method for the preparation of condensation compounds having two furanic cycles. The method involves reacting a mixture containing substantially two moles of methyl-2-furan and one mole of a reaction component under acid or mineral acid conditions. The reaction component is chosen from the group consisting of aldehydes and ketones having monovalent substituent members. Leon et al is limited to methyl furans which are comparatively easy to condense and are notably different from diamines.

SUMMARY OF THE INVENTION

We have now invented a synthetic procedure for the synthesis of diamino difurfuryl compounds via a one-step, low-temperature reaction that does not require additional steps for the protection (blocking) of the amino functionalities in the reactant or the deprotection (unblocking) of the amino functionalities in an intermediate product to give the final product. The synthetic procedure disclosed is less complex and more efficient and, therefore, more economical than previously known procedures wherein the amino functionalities are protected by reaction with formic acid prior to coupling with the carbonyl compound.

The results reported indicate the importance of the acid concentration, the reaction temperature, and the reaction time to the successful employment of a one-step reaction procedure. Insufficient attention was given to these three factors in the prior art. Thus, it is clear that the conditions needed for the successful employment of a one-step synthetic procedure were not obvious nor could they be deduced from the prior art.

In accordance with this discovery, it is an object of the invention to provide an economical, efficient one step method for the production of difurfuryl diamines.

A further object of the invention is to provide a new method for the utilization of renewable resources, especially wood products, and thereby decrease dependence on petrochemical feedstocks.

DETAILED DESCRIPTION OF THE INVENTION

The reaction of furfurylamine with the carbonyl-containing compound (e.g., formaldehyde, acetaldehyde, acetone, furfural, and other aldehydes and ketones) is conducted in strong acid (e.g., 6N NCl). The acid reacts with the amine group converting it to the hydrochoride salt and prevents the possibility of the carbonyl-containing compound reacting at this site. In addition the acid acts as the catalyst for the coupling reaction that occurs at C-5 of the furfuryl ring, as outlined in the following reaction scheme:

The broad ranges of operation are as follows:

| Temperature: | $-10°$ C. to $100°$ C. |
|---|---|
| Pressure: | 1 to 10 atmospheres |
| Reactants: | furfurylamine and any aldehyde- or ketone-containing compound |
| Ratio of Reactants: | furfurylamine to carbonyl-containing compound from 10:1 to 1:10 (mole:mole) |
| Catalyst: | any organic or mineral acid |
| Catalyst Concentration: | 0.1N to concentrated (>16N) |
| Catalyst to Furfurylamine Ratio: | 0.1:1 to 20:1 (wt:wt) |
| Reaction Time: | 0.1 minute to 48 hours |

Following is a list organic and mineral acids which may be used to practice the invention, however the following list is not intended to limit the acids which may be used to practice the invention in any way. Other acids will be known to those that are skilled in the art. Organic acids may include, among others, acetic acid, formic acid, carbonic acid, and lactic acid. Mineral acids may include, among others, nitric acid, phosphoric acid, hydrochloric acid, and sulfuric acid.

The preferred ranges of operation are as follows.

| Temperature: | 15 to $50°$ C. |
|---|---|
| Pressure: | 1 atmosphere |
| Reactants: | furfurylamine and acetaldehyde |
| Ratio of Reactants: | furfurylamine to acetaldehyde 2:1 (mole:mole) |
| Catalyst: | hydrochloric acid |
| Catalyst Concentration: | 6N |
| Catalyst to Furfurylamine Ratio: | 0.6:1 to 2.4:1 (wt:wt) |
| Reaction Time: | 10 to 90 minutes |

The employment of the invention is given by way of the following generalized synthetic procedure: 10 g. furfurylamine is placed in a 300 ml 3-necked flask equipped with a magnetic stirring bar. The flask is placed in an icebath. 75 ml of 6N HCl (a 50% vol:vol solution of concentrated HCl in water) is added slowly to permit the heat of neutralization to be absorbed by the icebath. A carbonyl-containing compound (0.055 mol.) is added rapidly. At this point, the reaction mixture is usually a faint brown color. The flask is removed from the icebath and allowed to warm to room temperature. As the reaction progresses, the intensity of the color gradually increases. After one hour the flask is cooled in an icebath and 75 ml. of 6N NaOH is slowly added to neutralize the HCl. This addition results in the separation of a viscous, amber-colored oil from the aqueous phase. The oil is recovered by extraction with an organic solvent (e.g., chloroform). The extract is dried over $MgSO_4$ and evaporated to yield the final product.

It is obvious from this generalized example that the reaction can be scaled to any size desired and that any of a large number of carbonyl-containing compounds (i.e., aldehydes and ketones) constitute possible reactants. It is also obvious that the quantities of acidic catalysts and basic solutions used will depend upon several factors, including temperature, reactants, desired results, and the like. Those skilled in the art will be able to determine a sufficient quantity and amount of basic solution to adequately neutralize the acidic catalyst chosen. Specific examples of such reactions are given below but are not meant in any way to limit the size of the reaction, the exact conditions employed in the reaction, or the nature of the carbonyl-containing reactant.

The invention will be further described by way of example only with reference to the following non-limiting Examples.

EXAMPLE 1

Preparation of 5,5'-methylenedifurfurylamine (MDFA): furfurylamine and formaldehyde (as a 37 wt % solution) were reacted in a manner similar to the generalized synthesis described above. The reaction product, as analysed by $^1$H- and $^{13}$C-NMR consisted of a 1:1 mixture of furfurylamine and 5,5'-methylenedifurfurylamine. The furfurylamine is stripped from the reaction mixture by vacuum distillation to give the final product. The identity of the final product was confirmed by $^1$H- and $^{13}$C-NMR and mass spectral analysis and comparison with the product produced by the alternate method described in U.S. Pat. No. 4,496,751.

MDFA

EXAMPLE 2

Preparation of 5,5'-ethylidenedifurfurylamine (EDFA): furfurylamine and acetaldehyde were reacted in a manner similar to the generalized synthesis described above. The reaction product, as analysed by $^1$H- and $^{13}$C-NMR consisted of a 1:9 mixture of furfurylamine and 5,5'-ethylidenedifurfurylamine. The furfurylamine is stripped from the reaction product by vacuum distillation to give the final product. The identity of the final product was confirmed by $^1$H- and $^{13}$C-NMR, IR, and mass spectral analysis and comparison with the product produced by the alternate method described in U.S. Pat. No. 4,496,751.

EDFA

Initially lengthy reaction times (typically 24 hr) were employed for the reaction of furfurylamine and formaldehyde in 6N HCl. However, the low yields and large amounts of polymeric material produced in the reaction led to the suspicion that these long reaction times were undesirable. A kinetic study of the condensation of furfurylamine with carbonyl compounds was undertaken to test this suspicion.

$^1$H-NMR spectroscopy proved to be the most useful and informative technique for the kinetic studies. Because of the availability of deuterated hydrochloric acid, the carbonyl condensation reactions of furfurylamine may be observed in-situ via proton NMR. By integrating the proton spectra, one can estimate the concentrations of reactants and products as functions of time. The kinetics of the reactions of furfurylamine with formaldehyde, acetaldehyde, and acetone were studied with this technique. The results are summarized below.

Figure 1:
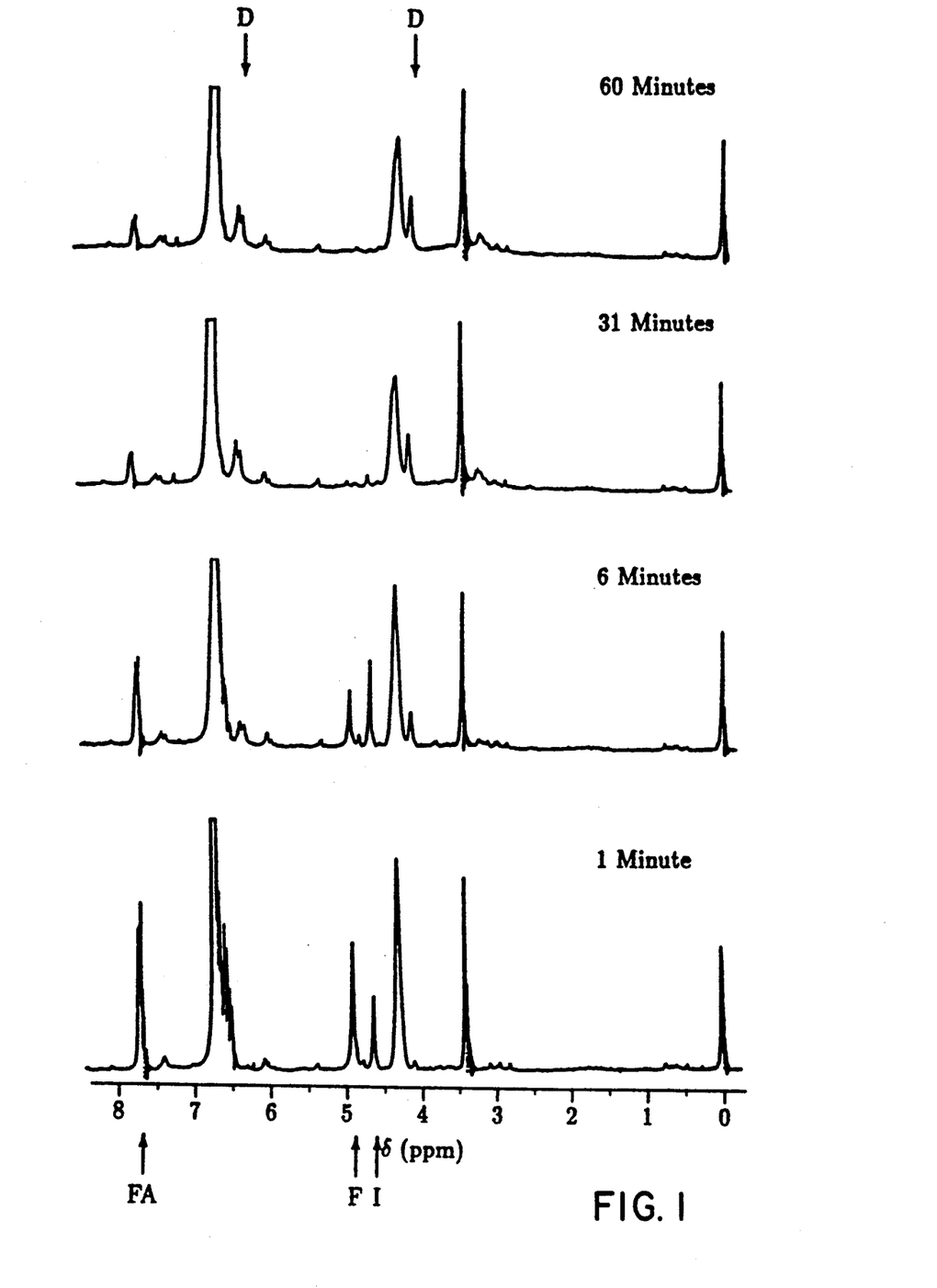
FIG. 1. In-situ observation of furfurylamine-formaldehyde reaction.

FIG. 1 contains proton NMR spectra of a mixture of furfurylamine and formaldehyde recorded 1, 6, 31, and 60 minutes after initiation of the reaction. The ratio of furfurylamine to formaldehyde was 2:1. The reaction was performed at a temperature of 35° C., and the spectra were collected on a Varian T-60 spectrometer. The peaks labeled FA, F, D, and I correspond, respectively, to resonances of furfurylamine, formaldehyde, the diamino product, and an intermediate of the reaction. The peaks at 0, 0.6, 1.75, and 3 ppm are resonances of the reference compound sodium 2,2-dimethyl-2-silapentane-5-sulfonate.

These spectra indicate that the reaction of furfurylamine and formaldehyde is very rapid under these conditions. The spectra which were recorded after 31 and 60 minutes are almost identical. Hence, the reaction was essentially complete after 31 minutes. The identity of the reaction intermediate which is observed is not known. It is believed to be an intermediate in the mechanistic pathway to the difurfuryl diamine.

As the reaction progresses, a broad resonance appears at 3.2 ppm. This peak is not a resonance of the diamino product. The compound giving rise to this resonance probably accounts for the observed loss of approximately 20% of the furanic starting material during this reaction.

At longer reaction times, such as several hours or longer, the difurfuryl diamino product is converted to other products.

Figure 2:
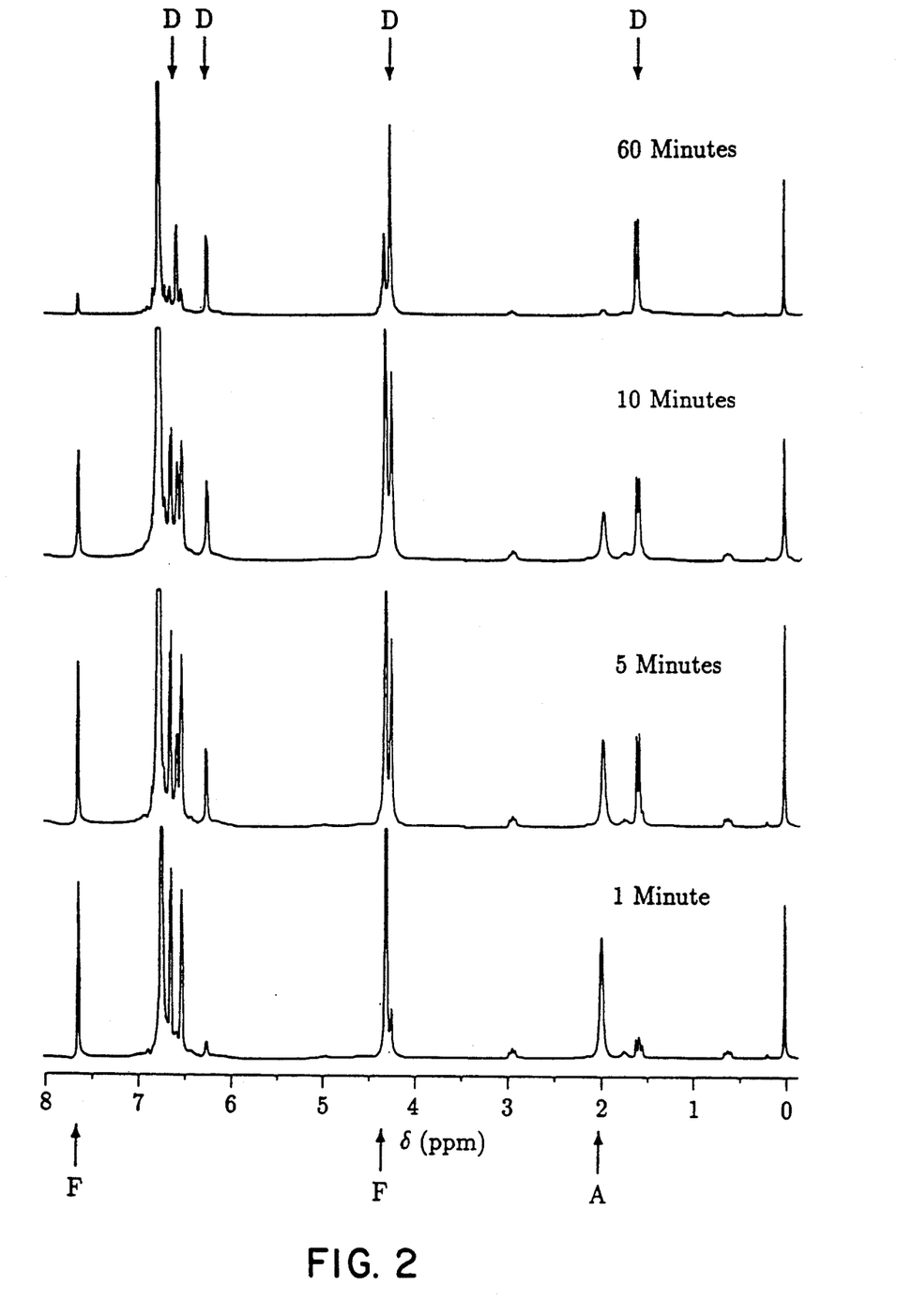
FIG. 2. In-situ observation of furfurylamine-acetaldehyde reaction.
Figure 3:
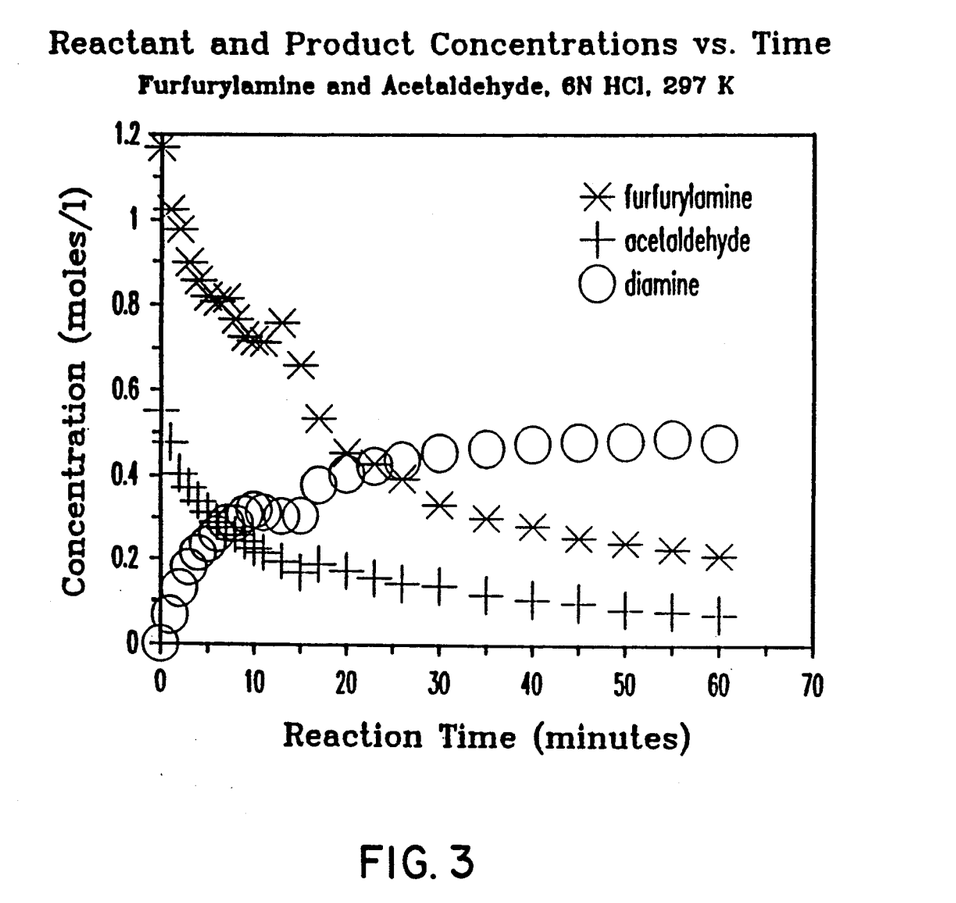
FIG. 3. Kinetic plot from furfurylamine-acetaldehyde reaction.
Figure 4A:
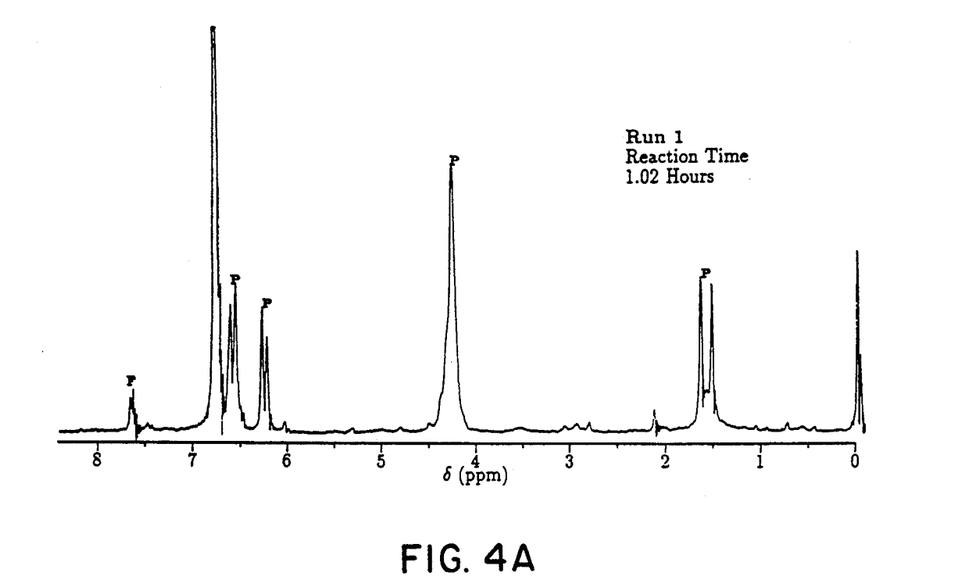
FIGS. 4A, 4B, 4C, and 4D. $^1$H-NMR spectra collected after 1 hour.
Figure 4B:
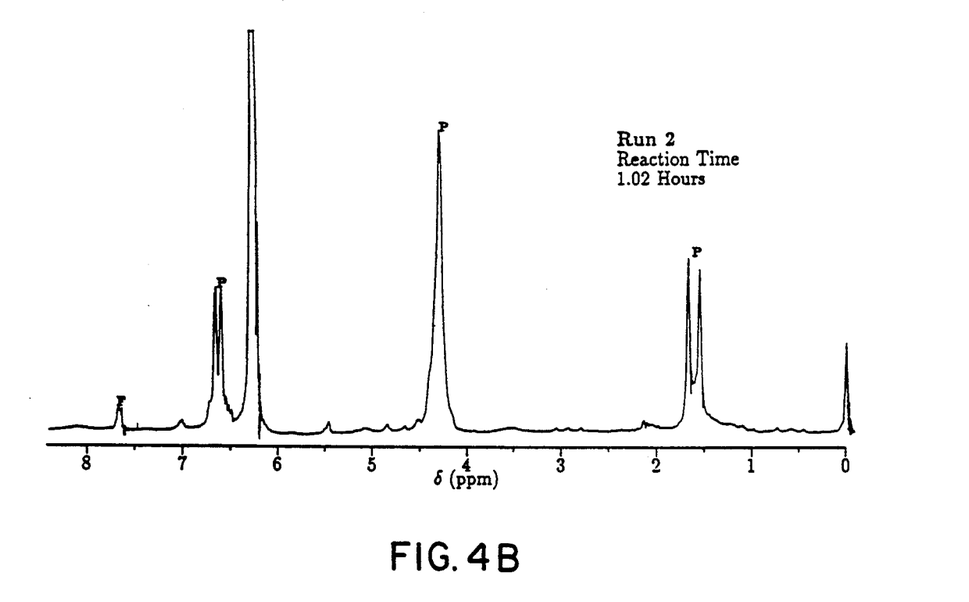
Figure 4C:
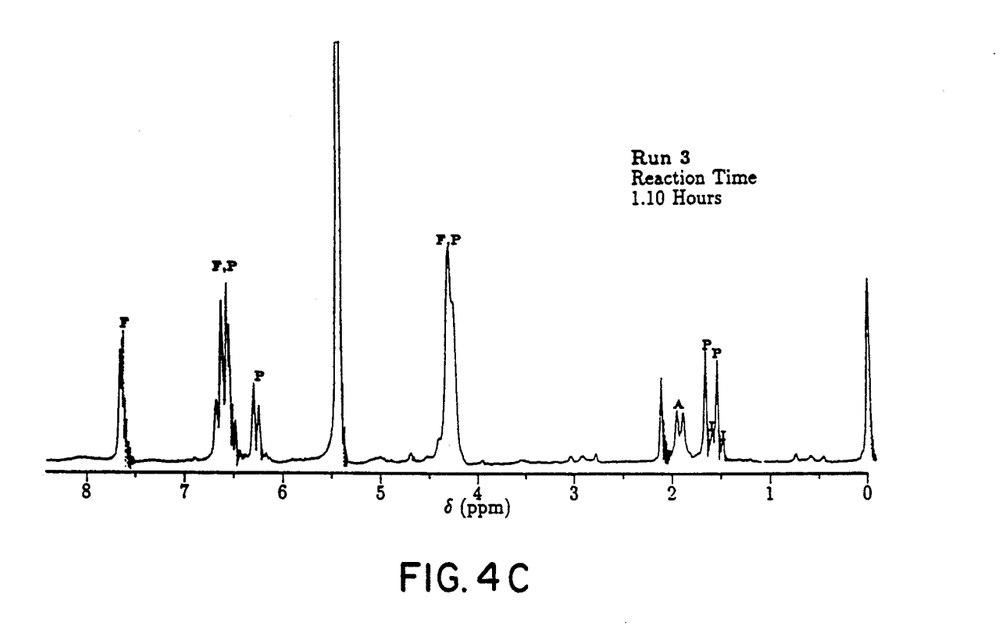
Figure 4D:
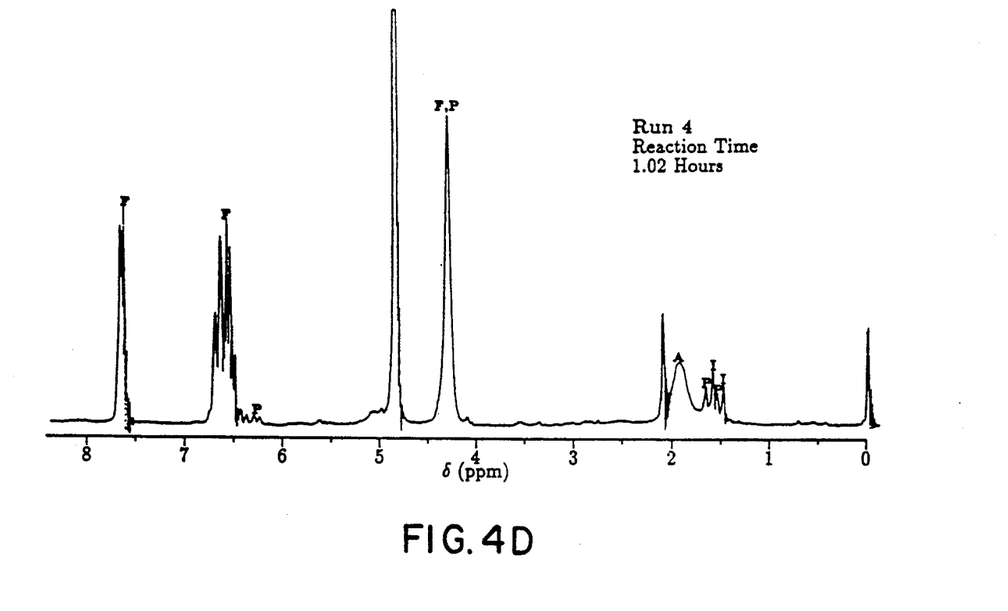

FIG. 2 contains proton NMR scans of a reaction mixture of furfurylamine and acetaldehyde taken 1, 5, 10, and 60 minutes after initiation of the reaction. The ratio of furfurylamine and acetaldehyde in this experiment was 2:1 (stoichiometric). The peaks labeled F, A, and D denote resonances of furfurylamine, acetaldehyde, and the difurfuryl diamino (EDFA) product respectively. The peaks at 0, 0.6, 1.75, and 3 ppm are resonances of the reference compound sodium 2,2-dimethyl-2-silapentane-5-sulfonate. These spectra were obtained on a Bruker WM-250 spectrometer. The reaction was performed at a temperature of 24° C. Plots of reactant and product concentrations vs. reaction time from the same experiment are provided in FIG. 3. The reaction of furfurylamine with acetaldehyde is remarkably rapid. Within the first 60 minutes, the reaction goes to completion. In fact, the data in FIG. 3 indicate that most of the starting material reacts within the first 30 minutes. From FIG. 2, one may observe that all of the peaks which are becoming larger with the progression of time are resonances of the diamino product. This demonstrates the selectivity of the reaction under these conditions for the desired difurfuryl diamino product.

At longer reaction times, EDFA is converted to other products. These decomposition products are most likely the result of an acidic cleavage of one or both of the furan rings of EDFA. The appearances after 2 weeks of resonances above 200 ppm (a region of the $^{13}$C-NMR spectrum most often assigned to carbonyl groups) in the $^{13}$C-NMR spectrum of the reaction mixture is consistent with this theory. Regardless of the products formed, this decomposition reaction progresses too slowly to pose any significant problems.

When examining the effect of acid on the furfurylamine-acetaldehyde condensation reaction, one must consider both the concentration of acid and the stoichiometric amount of acid in solution. For a given quantity of furfurylamine, the same amount of acid (on a molar basis) may give a completely different reaction rate and/or product distribution depending on its concentration in solution. The amino group of furfurylamine neutralizes a portion of the acid. Hence, it is also important to consider the molar ratio of furfurylamine to acid which is employed. It is only the free acid, that is, the amount of acid which is in excess of that required to convert furfurylamine to its hydrochloride salt, which is available for catalytic purposes.

A $2^2$ full factorial experiment was performed to examine the effect of acid. The factors which were used were the concentration of acid and the concentration of furfurylamine. The actual quantities of reactants which were used are summarized in Table 1. For each run, the reactants listed in Table 1 were combined in an NMR tube. The contents of each tube were then monitored via $^1$H-NMR for periods which ranged from 1 hour to several days. The contents of each tube were maintained at a temperature of 35° C. throughout the experiment.

TABLE 1

| | Quantities of Reactants Used ($2^2$ Factorial Design) | | | |
|---|---|---|---|---|
| Identification | Acid (HCl) (μL) | Furfurylamine (mg) | Acetaldehyde (μL) | Acid/ Furfurylamine Ratio |
| Run 1 | 500 of 6N | 66.7 | 20 | 4.37 |
| Run 2 | 500 of 6N | 133.4 | 40 | 2.18 |
| Run 3 | 500 of 3N | 66.7 | 20 | 2.18 |
| Run 4 | 500 of 3N | 133.4 | 40 | 1.09 |

FIG. 4 shows $^1$H-NMR spectra which were taken after a reaction time of approximately 1 hour; F denotes a resonance of furfurylamine, P denotes a resonance of product EDFA, A denotes a resonance of acetaldehyde, and I denotes a resonance of a proposed reaction intermediate. Resonances associated with the acetaldehyde molecule are absent in the spectra from Runs 1 and 2. This absence indicates that the reaction has gone essentially to completion in 1 hour or less under the conditions employed in these runs. The acetaldehyde resonance is still quite prominent after 1 hour of reaction under the conditions of Runs 3 and 4. In the case of Run 4, the EDFA resonance is small, indicating that little product has formed even after a reaction time of 1 hour.

TABLE 2

Effect of the amount and approximate concentration (assuming $\Delta V$ mixing = 0) of free acid on reaction rate

| Identification | Free acid (mmoles) | Free acid (moles/liter) | Relative reaction rate |
|---|---|---|---|
| Run 1 | 2.31 | 4.0 | Fast |
| Run 2 | 1.63 | 2.5 | Moderately fast |
| Run 3 | 0.81 | 1.4 | Intermediate |
| Run 4 | 0.13 | 0.2 | Slow |

As shown in Table 2, the rate of formation of product progressively decreases from Run 1 to Run 4; both the amount and the concentration of free acid also decrease in this same order. The concentrations of furfurylamine and acetaldehyde in Runs 2 and 4 were almost twice those used in Runs 1 and 3. Hence, one would logically expect enhanced rates under the conditions of Runs 2 and 4. However, the additional furfurylamine removes a proportionate amount of acid from solution. As a result, the free acid concentration was lower for Run 2 than for Run 1. Likewise, the rate of reaction was lower in Run 2 than in Run 1. The same trend was observed between Run 3 and Run 4. The effect of a lower free acid concentration more than offsets the expected enhancement in reaction rate due to the use of higher reactant concentrations.

Figure 5:
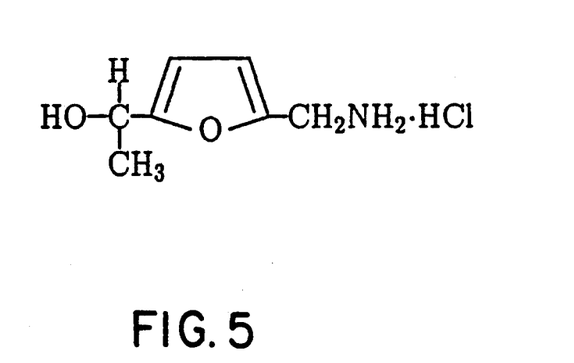
FIG. 5. Proposed intermediate in furfurylamine-acetaldehyde condensation reaction.
Figure 6A:
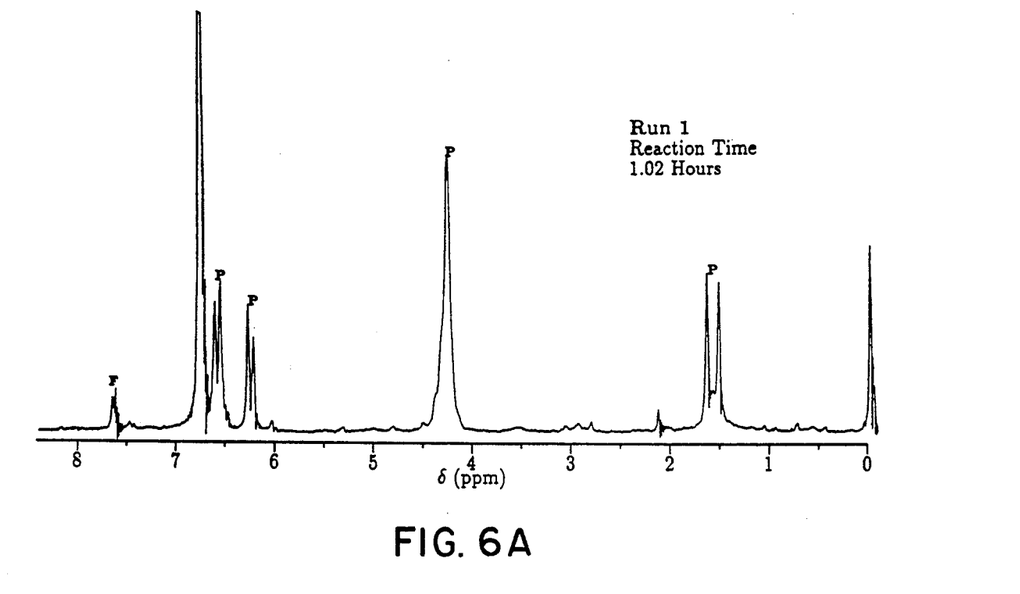
FIGS. 6A, 6B, 6C, and 6D. $^1$H-NMR spectra collected after completion of reaction.
Figure 6B:
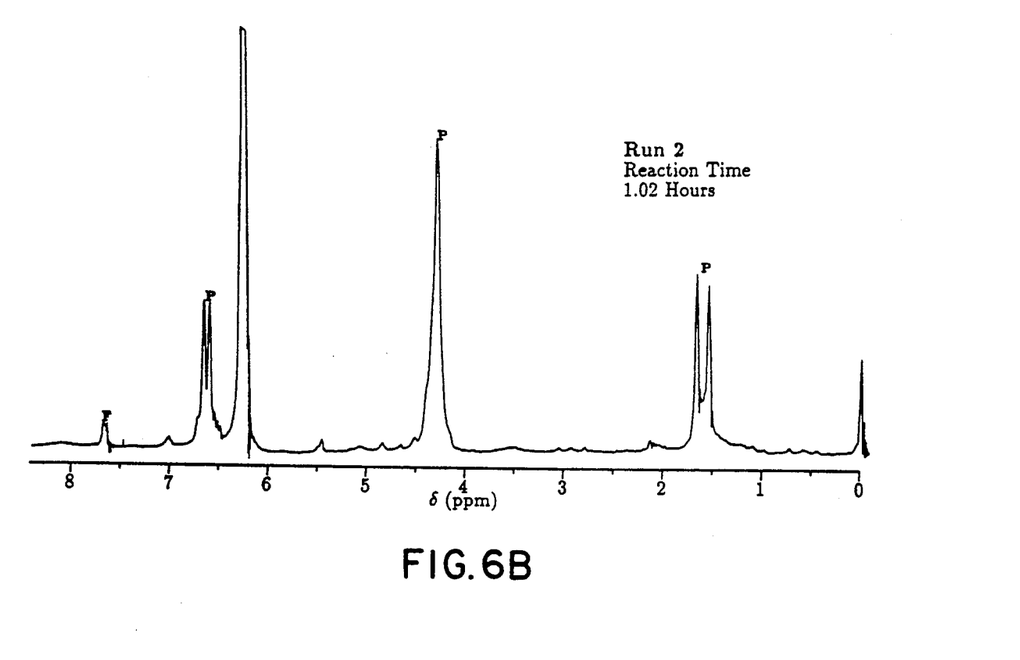
Figure 6C:
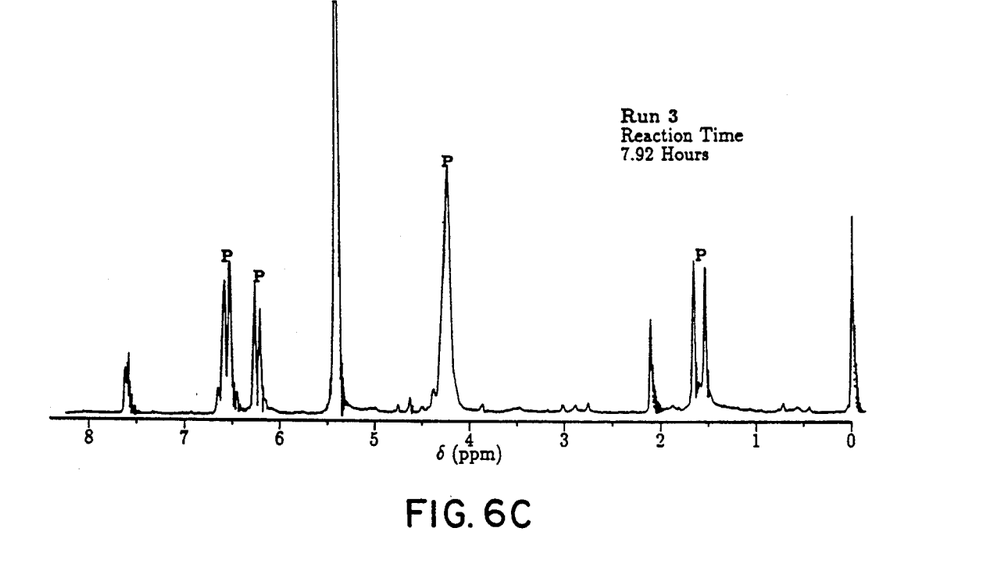
Figure 6D:
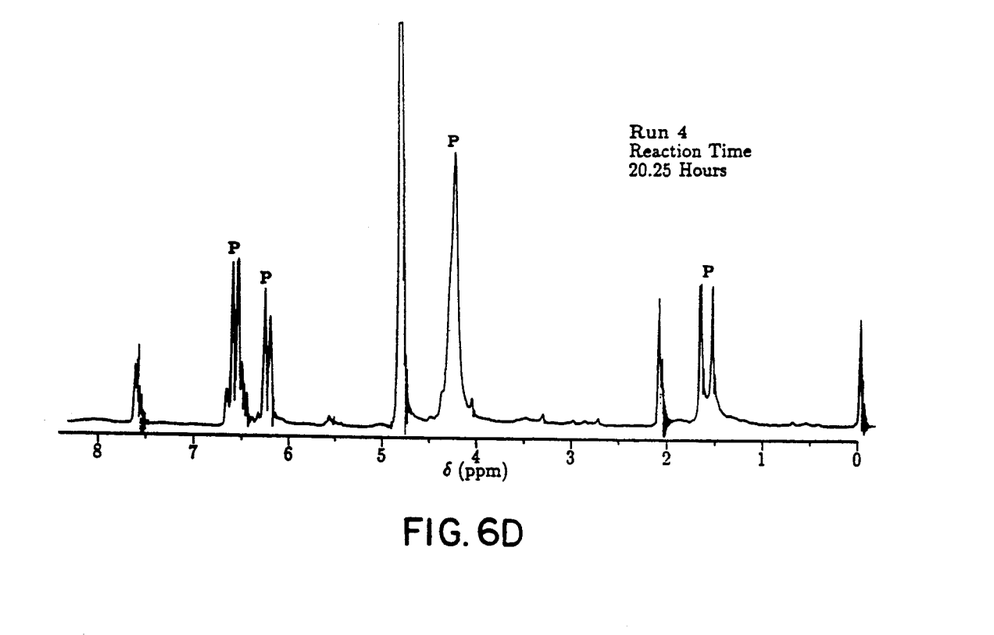

The spectra of Runs 3 and 4 in FIG. 4 contain peaks at approximately 1.5 ppm which are labeled I because they are believed to be resonances from a reaction intermediate. Based upon intermediates which have been proposed for mechanisms of similar carbonyl condensation reactions, the species giving rise to these resonances is believed to be the compound shown in FIG. 5. The observed doublet resonance occurs at a chemical shift (approximately 1.5 ppm) which is consistent with that expected for the methyl group of the compound in FIG. 5. The appearance and subsequent disappearance of a peak in the $^1$H-NMR spectrum would also be consistent with a side reaction which is at chemical equilibrium. Hence, neither the structure nor even the existence of a true reaction intermediate can be positively established via the use of the present $^1$H-NMR technique.

FIG. 6 shows the $^1$H-NMR spectra which were collected at the conclusion of each run. Those resonances which are associated with the product EDFA are again designated with the label P. Although there are observable differences between the four spectra, all are consistent with the presumption that EDFA is the major end product of the reaction. The amount of furfurylamine which does not react is greater for Runs 3 and 4 (lower concentrations of free acid were employed in these runs) than for Runs 1 and 2, as evidenced by the size of the multiplet peak at 7.6 ppm. The singlet peak at 2.15 ppm is also observed in $^1$H-NMR spectra of solutions of acetaldehyde in various concentrations of HCl. The species which gives rise to this resonance has not been identified. This peak becomes more prominent as the concentration of acid decreases.

To corroborate the results of the $^1$H-NMR experiment, each run was repeated on a larger scale (employing 10 g of furfurylamine). A product was isolated from these larger scale reactions via neutralization with NaOH and extraction with chloroform. $^1$H-NMR spectra, $^{13}$C-NMR spectra, and GC- mass spectra were obtained for the isolated products. With the exception of the reaction which was conducted under the conditions of Run 4, which had the lowest concentration of free acid, the isolated products yielded spectra which were consistent with those of EDFA accompanied by some unreacted furfurylamine. Although the product of the reaction conducted at the lowest concentration of free acid contained some EDFA, it also contained at least two observable side products. One of these is believed to be the Schiff base. It is believed that the presence of side products in the final product of the reaction was a result of insufficient reaction time, leading to an incomplete reaction, rather than because of some underlying chemical equilibrium or alternate reaction pathway.

The results may be summarized as follows: the rate of condensation of furfurylamine with acetaldehyde decreases as the concentration of free acid decreases; the quantity of unreacted furfurylamine increases as the free acid concentration decreases; and the ultimate distribution of reaction products, with the possible exception of reaction at very low free acid concentrations, is relatively insensitive to the concentration of free acid. However, the yield of EDFA is slightly lower when less acid is present.

A one step method for the preparation of difurfuryl diamines is disclosed which is both more efficient and economical and less complex than the methods previously well known in the art.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A one step method for the production of difurfuryl diamines comprising:
   reacting unprotected furfurylamine with a carbonyl-containing compound in the presence of a catalyst wherein said furfurylamine to said catalyst is in a weight:weight ratio ranging from 0.1:1 to 20:1, wherein the concentration of said catalyst is between 0.1N to 16N, wherein said one step method is performed at temperature ranges from −10° C. to 100° C., and wherein the reaction time ranges from 0.1 minute to 48 hours.

2. The one step method as claimed in claim 1 wherein said difurfuryl diamines are mixed with a basic solution.

3. The one step method as claimed in claim 1 wherein any oil produced is extracted from said difurfuryl diamines.

4. The one step method as claimed in claim 1 wherein said carbonyl-containing compounds are selected from the group consisting of aldehydes, ketones and furfural.

5. The one step method as claimed in claim 4 wherein said carbonyl-containing compounds are selected from the group consisting of formaldehyde, acetaldehyde, and acetone.

6. The one step method as claimed in claim 5 wherein said carbonyl-containing compound is acetaldehyde.

7. The one step method as claimed in claim 1 wherein said catalyst is selected from the group consisting of organic and mineral acids.

8. The one step method as claimed in claim 7 wherein said catalyst is hydrochloric acid.

9. The one step method as claimed in claim 1 wherein said catalyst concentration is from between 4N to 8N.

10. The one step method as claimed in claim 1 wherein said catalyst concentration is 6N.

11. The one step method as claimed in claim 1 wherein the temperature ranges from 15° C. to 50° C.

12. The one step method as claimed in claim 1 wherein said furfurylamine and said carbonyl-containing compounds are in a mole:mole ratio ranging from 10:1 to 1:10.

13. The one step method as claimed in claim 12 wherein said furfurylamine and said carbonyl-containing compounds are in a mole:mole ratio of 2:1.

14. The one step method as claimed in claim 1 wherein said furfurylamine to said catalyst is in a weight:weight ratio ranging from 0.6:1 to 2.4:1.

* * * * *